US012788492B2

(12) United States Patent
Palliyali et al.

(10) Patent No.: US 12,788,492 B2
(45) Date of Patent: Nov. 10, 2026

(54) SYSTEM AND METHODS FOR MIXED REALITY SURGICAL SIMULATION

(71) Applicant: Hamad Medical Corporation, Doha (QA)

(72) Inventors: Ahammed Waseem Palliyali, Doha (QA); Santu Paul, Doha (QA); Julien Abi Nahed, Doha (QA); Abdulla Al-Ansari, Doha (QA); Nikhil Navkar, Doha (QA)

(73) Assignee: HAMAD MEDICAL CORPORATION, Doha (QA)

( * ) Notice: Subject to any disclaimer, the term of this patent is extended or adjusted under 35 U.S.C. 154(b) by 156 days.

(21) Appl. No.: 18/866,839

(22) PCT Filed: May 18, 2023

(86) PCT No.: PCT/QA2023/050007
§ 371 (c)(1),
(2) Date: Nov. 18, 2024

(87) PCT Pub. No.: WO2023/224504
PCT Pub. Date: Nov. 23, 2023

(65) Prior Publication Data

US 2025/0195144 A1 Jun. 19, 2025

Related U.S. Application Data

(60) Provisional application No. 63/364,986, filed on May 19, 2022.

(51) Int. Cl.

| | |
|---|---|
| ***A61B 34/10*** | (2016.01) |
| ***A61B 34/20*** | (2016.01) |

(52) U.S. Cl.
CPC .............. *A61B 34/10* (2016.02); *A61B 34/20* (2016.02); *A61B 2034/105* (2016.02); *A61B 2034/2055* (2016.02)

(58) Field of Classification Search
None
See application file for complete search history.

(56) References Cited

U.S. PATENT DOCUMENTS

| | | | |
|---|---|---|---|
| 2004/0234933 | A1 | 11/2004 | Dawson et al. |
| 2013/0157239 | A1 | 6/2013 | Russo |

(Continued)

FOREIGN PATENT DOCUMENTS

| | | | | | |
|---|---|---|---|---|---|
| CA | 3103562 | C * | 4/2022 | ............. | G06T 11/00 |
| FR | 3078624 | A1 * | 9/2019 | ............. | A61B 34/20 |
| WO | WO-2020197422 | A2 * | 10/2020 | ........... | A61B 90/361 |

OTHER PUBLICATIONS

Extended European Search Report for related European Application No. 23807986.7; action dated Mar. 30, 2026; (11 pages).

(Continued)

*Primary Examiner* — James B Hull
(74) *Attorney, Agent, or Firm* — K&L Gates LLP

(57) ABSTRACT

A system for mixed reality surgical simulation is provided. The system includes a simulator, an optical tracking system, an input device, a visualization screen, and a simulation workstation, wherein the simulation workstation renders an augmented view on the visualization screen.

5 Claims, 7 Drawing Sheets

(56) References Cited

U.S. PATENT DOCUMENTS

| | | | | |
|---|---|---|---|---|
| 2014/0329217 | A1* | 11/2014 | Barsness | G09B 23/285 434/272 |
| 2019/0005848 | A1* | 1/2019 | Garcia Kilroy | G09B 23/28 |
| 2021/0059755 | A1* | 3/2021 | Villain | A61B 34/10 |
| 2021/0233429 | A1 | 7/2021 | Barber et al. | |
| 2021/0369353 | A1* | 12/2021 | Nikou | A61B 34/20 |

OTHER PUBLICATIONS

International Search Report for related International Application No. PCT/QA2023/050007; action dated Nov. 23, 2023; (3 pages).

Written Opinion for related International Application No. PCT/QA2023/050007; action dated Nov. 23, 2023; (8 pages).

* cited by examiner

SYSTEM AND METHODS FOR MIXED REALITY SURGICAL SIMULATION

CROSS-REFERENCES TO RELATED APPLICATIONS

The present disclosure is a National Stage filing under 35 U.S.C. 371 of International Application No. PCT/QA2023/050007, filed May 18, 2023, which claims priority to U.S. Provisional Patent Application 63/364,986 titled "SYSTEM AND METHODS FOR MIXED REALITY SURGICAL SIMULATION" having a filing date of May 19, 2022, the entirety of which is incorporated herein.

BACKGROUND

Minimally invasive surgeries ("MIS") have become a prominent method for many surgical procedures. As compared to traditional open surgery, which involves large incisions to gain direct access to the surgical site, MIS use small incisions to enter elongated surgical instruments to operate on the surgical site. This may result in surgical benefits, including shorter recovery time, smaller external scarring, and lower discomfort. To efficiently perform MIS, the surgeon should understand both the anatomy at the surgical site and the tool-tissue interaction required to operate such surgical site. Thus, before performing MIS, many surgeons use box trainers with phantoms for replicating surgical sites or virtual reality ("VR") simulators. However, current technology has several disadvantages. For example, box trainers lack realism in illustrating a surgical site with its surroundings of the cavity. Further, VR simulators lack realistic tool-tissue interaction in any of the basic surgical tasks, such as cutting, suturing, and cauterizing. Improved system and methods for surgical training are therefore needed.

SUMMARY

In light of the disclosure herein and without limiting the disclosure in any way, in a first aspect of the present disclosure, which may be combined with any other aspect listed herein unless specified otherwise, a system for mixed reality surgical simulation is provided. The system includes a simulator, an optical tracking system, an input device, a visualization screen, and a simulation workstation, wherein the simulation workstation renders an augmented view on the visualization screen.

In accordance with a second aspect of the present disclosure, which may be used in combination with any other aspect listed herein unless stated otherwise, the optical tracking system acquires tracking data and the simulator acquires video stream data.

In accordance with a third aspect of the present disclosure, which may be used in combination with any other aspect listed herein unless stated otherwise, the input device transmits a plurality of user inputs to the simulation workstation.

In accordance with a fourth aspect of the present disclosure, which may be used in combination with any other aspect listed herein unless stated otherwise, the simulation workstation includes a video module configured to receive video stream data, a tracking module configured to receive tracking data, and a user interfacing module configured to receive the plurality of user inputs.

In accordance with a fifth aspect of the present disclosure, which may be used in combination with any other aspect listed herein unless stated otherwise, the simulation workstation further includes a core processing module configured to process video stream data, tracking data, and the plurality of user inputs, wherein the core processing module transmits video stream data, tracking data, and the plurality of user inputs to a graphical rendering module.

In accordance with a sixth aspect of the present disclosure, which may be used in combination with any other aspect listed herein unless stated otherwise, the graphical rendering module renders an augmented view on the visualization screen.

In accordance with a seventh aspect of the present disclosure, which may be used in combination with any other aspect listed herein unless stated otherwise, the simulator includes a scope system, a box tracking frame, a chroma background, an aperture configured to receive an instrument, a configuration table configured to receive a tissue, and an ambient light.

In accordance with an eighth aspect of the present disclosure, which may be used in combination with any other aspect listed herein unless stated otherwise, the scope system includes a tracking frame.

In accordance with a ninth aspect of the present disclosure, which may be used in combination with any other aspect listed herein unless stated otherwise, the simulator is a box simulator.

In light of the disclosure herein and without limiting the disclosure in any way, in a second aspect of the present disclosure, which may be combined with any other aspect listed herein unless specified otherwise, a method of mixed reality surgical simulation is provided. The method includes the steps of positioning a simulator in front of an optical tracking system; activating a simulation workstation, an optical tracking system, and a scope system, wherein the a box tracking frame of the simulator is in a field of view of the optical tracking system; loading a virtual tissue model onto the simulation workstation; placing the virtual tissue model in a virtual environment based on the tracking frame of the simulator; placing a virtual camera in the virtual environment, wherein the virtual camera matches a relative pose of a tracking frame of the scope system; configuring a plurality of parameters using an input device; placing a 3D-printed tissue on a configuration table of the simulator; inserting a surgical instrument into the simulator; and performing a surgical task.

In accordance with an eleventh aspect of the present disclosure, which may be used in combination with any other aspect listed herein unless stated otherwise, the core processing module executes chroma keying on the video stream data to remove a background in the video stream data in real-time.

In accordance with a twelfth aspect of the present disclosure, which may be used in combination with any other aspect listed herein unless stated otherwise, the graphical rendering module places the video stream data with the background removed in the virtual environment at the frustum of the virtual camera and renders the view on a visualization screen.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

To efficiently perform MIS, a surgeon should understand both the anatomy at the surgical site and the tool-tissue interaction required to operate such surgical site. Thus, for training, many surgeons use box trainers or VR simulators. However, current technology has several disadvantages. For example, box trainers lack realism in illustrating a surgical site while VR simulators lack realistic tool-tissue interaction in any of the basic surgical tasks. These disadvantages may lead to a suboptimal learning experience for surgeons. Thus, aspects of the present disclosure may address the above discussed disadvantages in current training techniques.

The present disclosure generally relates to systems and methods for mixed reality training simulators. The mixed reality systems may be used to train specific procedures that are used in MIS. In an example embodiment, the system includes a simulator, a simulation workstation, an optical tracking system, an input device, and a visualization screen. The simulator may further include a scope system, a box tracking frame, a chroma background, and an aperture to insert various instruments used in MIS. The simulator may also include a configuration table to hold 3D printed tissue and an ambient light. While in use, the scope system of the simulator acquires a video stream and the optical tracking system acquires tracking data. The tracking data and the video stream are transmitted to the simulation workstation. The input device is used to configure the setting of the simulation workstation. The simulation workstation processes the user input from the input device, the tracking data from the optical tracking system, and the video stream from the scope system to render an augmented view on the visualization screen.

In various embodiments, the simulation workstation is a laptop that is configured to run various software modules. In an example, the software modules are implemented using C++. Further, the graphical rendering may be performed using VTK whereas the GUI implemented may use Qt. The threaded implementation of the modules can be performed using Boost, and the simulation workstation is realized on a standard PC with an integrated graphics processing unit. The optical tracking system that may be used can be implemented on V120: Trio OptiTrack motion capture system by NaturalPoint, Inc. The tracking data can be processed using an OptiTrack software platform, which runs the operating room workstation. The removal of the green background on the box simulator is done using a chroma key filter using OpenCV library.

Figure 1:
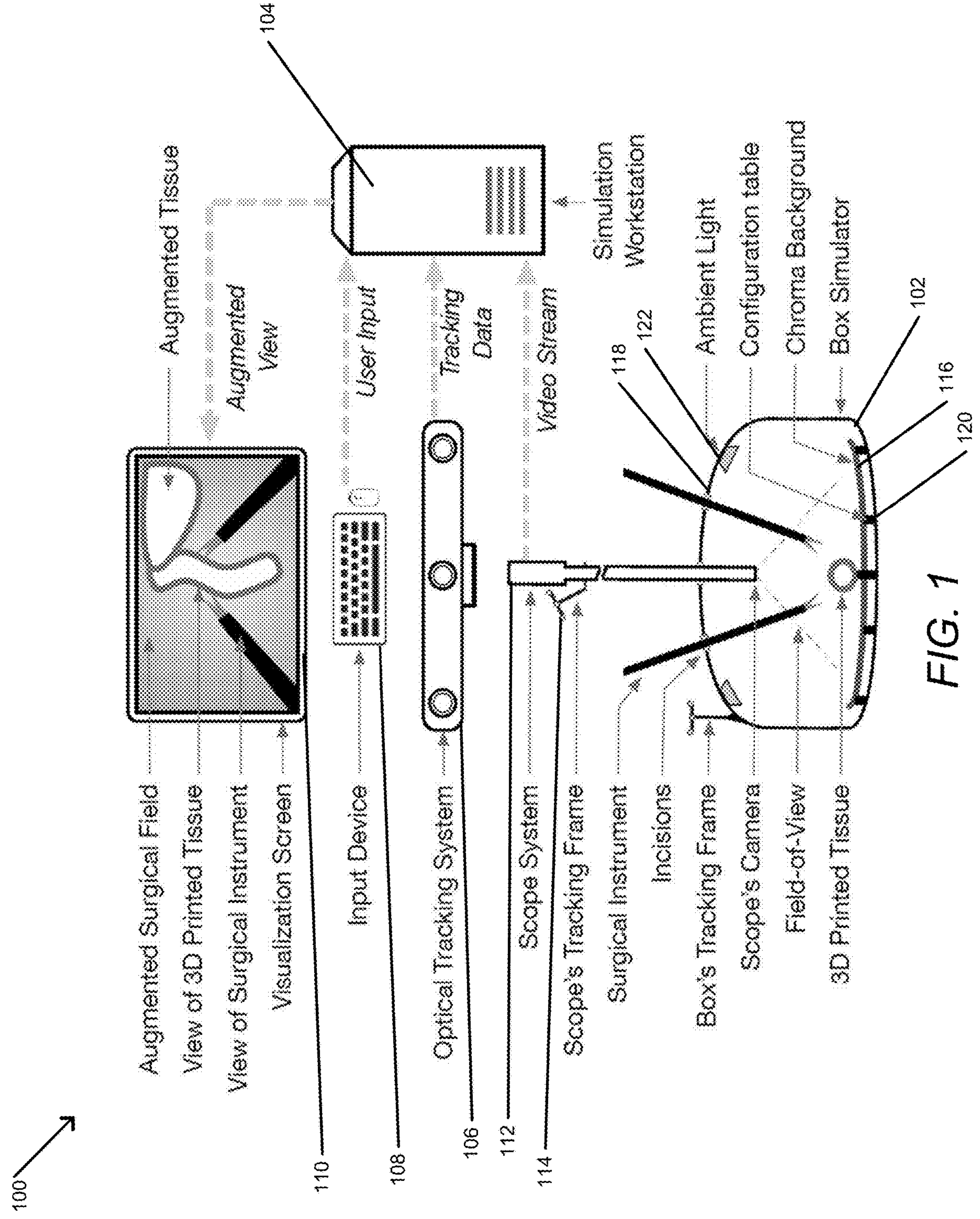
FIG. 1 illustrates a system for mixed reality surgical simulation, according to various examples of the present disclosure.

FIG. 1 illustrates a system for mixed reality surgical simulation, according to various examples of the present disclosure. The system 100 includes a simulator 102, a simulation workstation 104, an optical tracking system 106, an input device 108, and a visualization screen 110. The simulator 102 includes a scope system 112, a box tracking frame 114, a chroma background 116, and an aperture 118 to insert various instruments used in MIS. The simulator 102 further includes a configuration table 120 to hold 3D printed tissue and an ambient light 122. While in use, the scope system 112 of the simulator 102 acquires a video stream and the optical tracking system 106 acquires tracking data. The tracking data and the video stream are transmitted to the simulation workstation 104. The input device 108 is used to configure the setting of the simulation workstation 104. The simulation workstation 104 then processes the user input from the input device 108; the tracking data from the optical tracking system 106; and the video stream from the scope system 112 to render an augmented view on the visualization screen 110.

Figure 2:
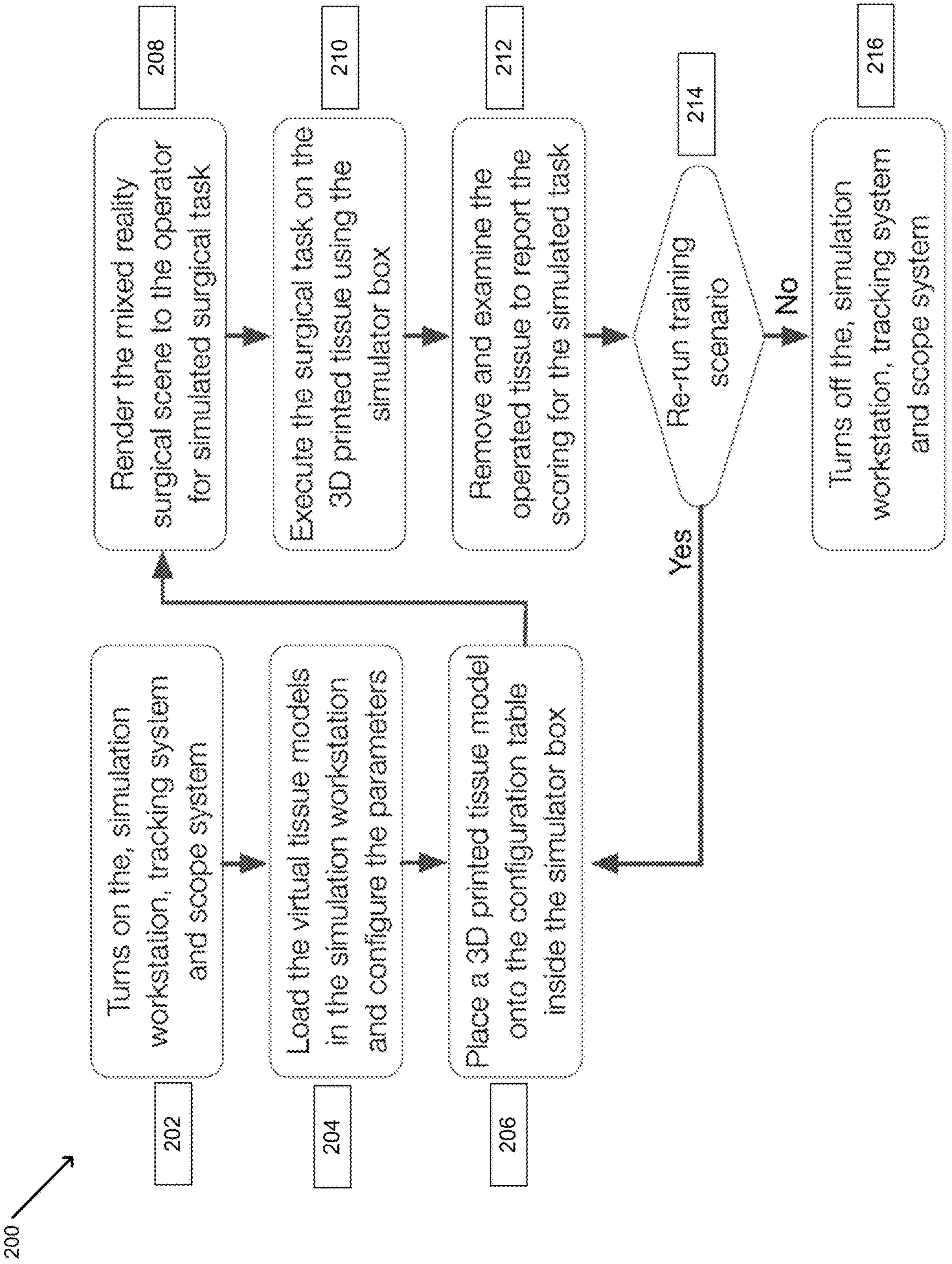
FIG. 2 illustrates a flow diagram of a system for mixed reality surgical simulation, according to various examples of the present disclosure.

FIG. 2 illustrates a flow diagram of a system for mixed reality surgical simulation, according to various examples of the present disclosure. Within the flow diagram 200, a user first positions the simulator in front of the optical tracking system, such that the box tracking frame and the scope tracking frame are visible. Then, the user may turn on the simulation workstation, the optical tracking system, and the scope system 202. Next, the user may load the virtual tissue model onto the simulation workstation and configure the parameters using the input device 204. Once the virtual tissue model is loaded onto the simulation workstation and the parameters of the simulation workstation are configured, a user can place a 3D-printed tissue on the configuration table of the simulator and insert the surgical instruments into the simulator 206. A mixed-reality surgical scene is rendered on the visualization screen by the simulation workstation comprising 3D-printed tissue, a virtual surgical field in the background, virtual tissues in the foreground, and real surgical instruments 208.

The user may perform the surgical task on the 3D printed tissue within the simulator, which is continuously rendered as if it is immersed into a surgical field 210. At the end of the task, the user may remove and examine the operated tissue to report a score for the simulated task 212. At such point, the user can determine to re-run the training scenario 214. To perform the simulation task again, a new 3D printed tissue can be replaced on the configuration table 206. However, if a second simulation task is not performed, the user may turn off the system, including the simulation workstation, the optical tracking system, and the scope system 216.

Figure 3:
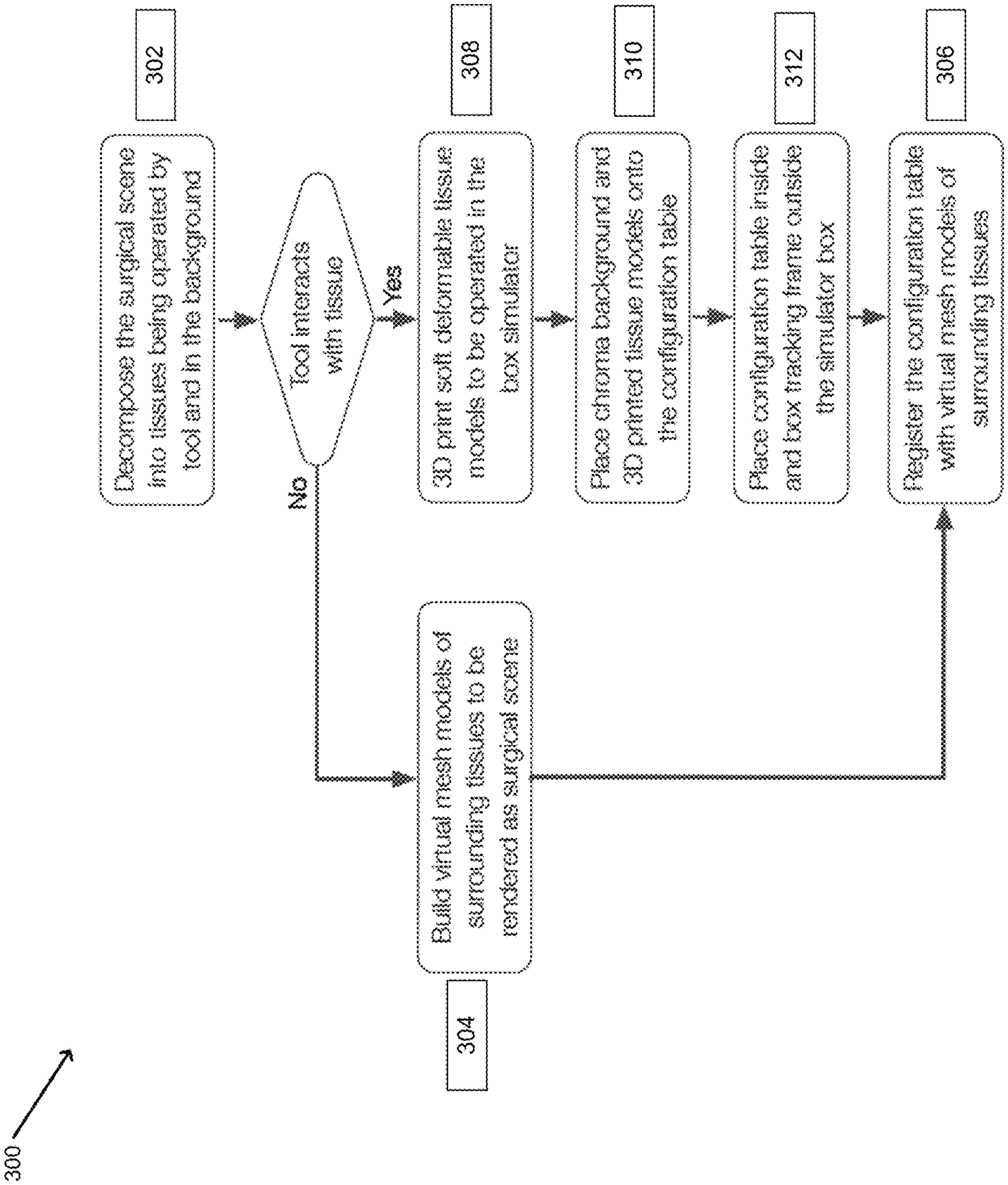
FIG. 3 illustrates a flow diagram of a set up for a system for mixed reality surgical simulation, according to various examples of the present disclosure.

FIG. 3 illustrates a flow diagram of a set up for a system for mixed reality surgical simulation, according to various examples of the present disclosure. Once a surgical scene is identified, the flow diagram 300 illustrates the system setup. The first step is to identify the different tissues involved at the surgical site (i.e. the tissues that are visible to the scope camera during its movement in a minimally invasive surgical setting). Then, the identified tissues must be classified into whether the surgical instrument will interact with them (such as cut, cauterized, sutured, grasped, etc.), or the tissues will be a part of the background/foreground scene to be rendered on the visualization screen. In other words, the surgical scene must be decomposed into tissues being operated by the tool versus tissues that are only in the background/foreground 302. If the tissues are a part of the background/foreground and have no active role in interacting with the surgical tooltips, virtual mesh models for these tissues are built and textures are mapped onto them from a real surgical scene 304. These tissues are rendered onto the surgical scene and, subsequently, the configuration table registers the virtual mesh models of the surrounding tissue 306. However, if the tools do interact with the tissues, a different procedure is followed.

Namely, this procedure involves starting with 3D printing soft deformable tissue models 308. The next step involves the careful placement of the 3D printed tissues onto the configuration table with a chroma background 310. The chroma background is a simple surface with a uniform color that is not present in any of the tissues. Common colors for chroma include green or blue. Once the chroma background and the tissues are in place, the configuration table is placed inside the simulator box 312. A box tracking frame is attached outside the simulator for registration purposes. A scope with another tracking frame is then inserted into the simulator. The virtual models are rendered in the virtual world based on the box tracking frame and the real tissues are also rendered in the virtual world using the output from the scope camera 306. The feed from the camera is processed to remove the chroma background leaving only the tissues and surgical instruments from the feed to be present in the virtual world. Both the box tracking frame and the scope tracking frame are used to register the virtual and 3D printed tissues in the virtual world. The rendering of both virtual and real tissues in the same space may depict a mixed reality system.

Figure 4:
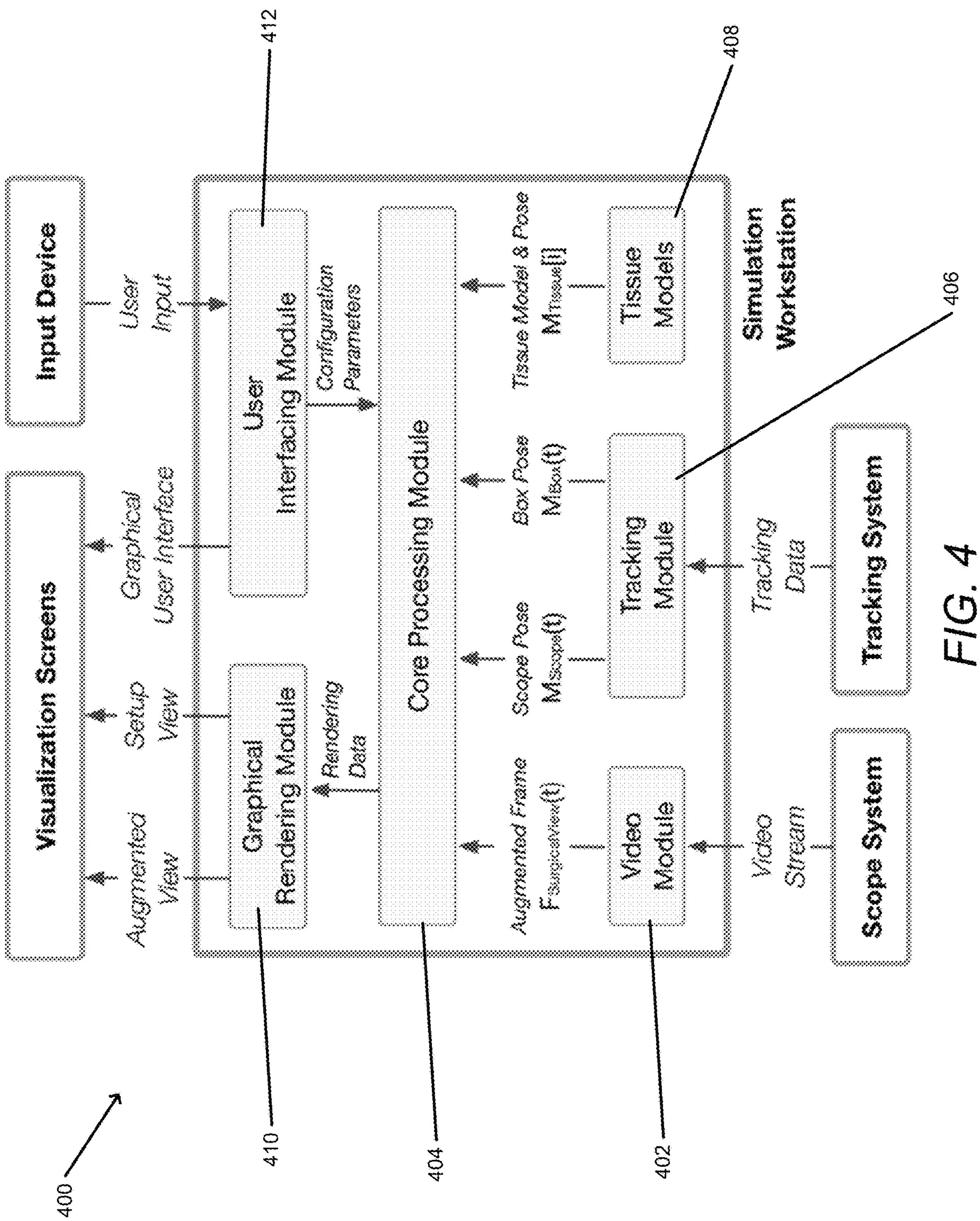
FIG. 4 illustrates various software modules for a system for mixed reality surgical simulation, according to various examples of the present disclosure.

FIG. 4 illustrates various software modules for a system for mixed reality surgical simulation, according to various examples of the present disclosure. The system 400 may include a video module 402. The video module 402 is configured to receive a video stream of the surgical field inside the simulator from the scope system. Once the video stream is received, the video module 402 processes the video stream, frame-by-frame, and sends the video frames to a core processing module 404. In an example embodiment, a video frame at time instant 't' is denoted by $F_{SurgicalView}(t)$. The video frame consists of a chroma background, surgical instruments, and 3D printed tissue models.

The system 400 may further include a tracking module 406. The tracking module 406 is configured to the tracking frame (with a unique arrangement of retroreflective markers) that is attached to the scope. The optical tracking system continuously sense the poses (position and orientation) of the tracking frames and sends the tracking data stream to the tracking module 406. The tracking module 406 then processes the stream and computes the pose of the scope camera and the simulator. In an example embodiment, the scope camera's pose at time instant 't' is represented by a 4×4 homogenous transformation $M_{Scope}(t)$. Whereas, the pose of the simulator is represented by $M_{Box}(t)$. $M_{Scope}(t)$ and $M_{Box}(t)$ may be measured with respect to the coordinate system of the optical tracking system inside the training room and are fed to the core processing module 404.

The system 400 may further include a tissue module 408. The tissue module 408 is configured to send the 3D meshes and their poses representing tissue models at the surgical site (operating field) to the core processing module 404. These meshes are specific to a simulation scene and loaded into the simulation system with predefined poses $M_{Tissue}[i]$ (where 'i' varies from 0 to the number of tissue models).

The system 400 may further include a core processing module 404. The core processing module 404 acts as a central core for processing data in the simulation workstation. The module receives data from the user-interfacing module, video module, tracking module, and tissue module and sends data to the graphical rendering module. The core processing module applies the chroma key filter to the video frame $F_{SurgicalView}(t)$ to segment and extract 3D printed tissue and surgical instruments. In other words, chroma keying may be performed. Registration of the segmented video frame is then performed with the 3D meshes fetched from the tissue module. The registration is performed using $M_{Scope}(t)$ and $M_{Box}(t)$ poses such that the segmented 3D printed tissue in the video frame aligns with the tissue models.

Figure 5A:
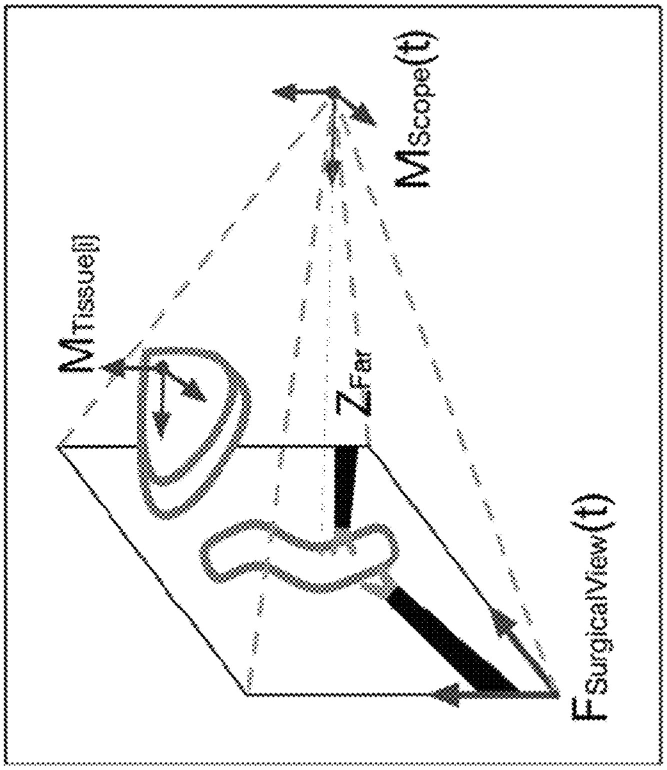
FIGS. 5A to 5B illustrate renderings of a surgical view video and tissue models, according to various examples of the present disclosure.
Figure 5B:
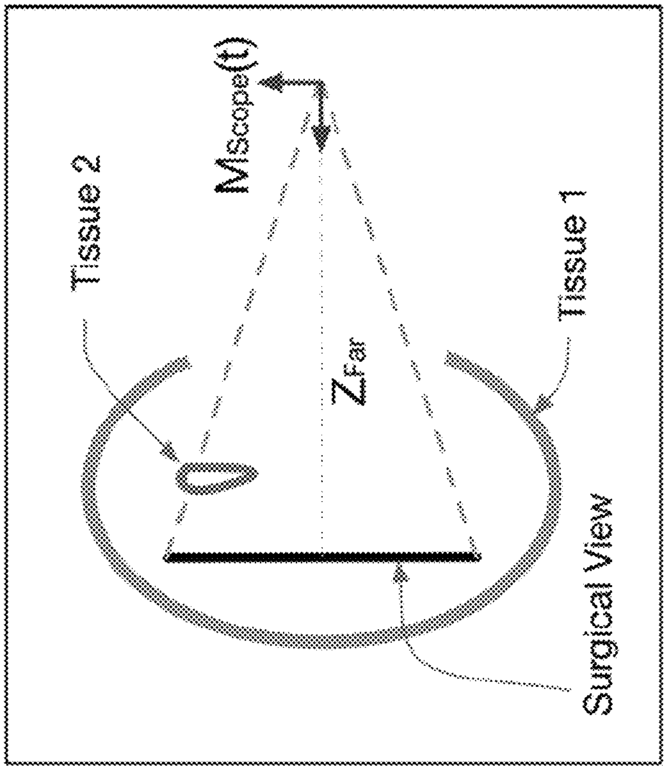

The system 400 may further include a graphical rendering module 410. The graphical rendering module 410 renders both the 3D meshes along with the video frame (segmented 3D printed tissue and surgical instruments) onto the visualization screen, creating an immersive mixed reality environment. A virtual camera frustum is rendered at $M_{Scope}(t)$ with the same configuration as the scope camera used in the simulator as illustrated in FIG. 5. The video frame $F_{SurgicalView}(t)$ is rendered on a plane in front of the $M_{Scope}(t)$. The $Z_{Far}$ (i.e. distance of the plane from the scope position along the viewing direction) is adjusted such that the plane of $F_{SurgicalView}(t)$ stays in between the rendered tissue models of the surgical scene. The illustration in FIG. 5 shows surgical view frame $Z_{Far}$ is adjusted such that 'Tissue 1' is in front of surgical view whereas 'Tissue 2' is rendered behind. Chroma-key filtering removes the background chroma color and makes it transparent by introducing an alpha channel. When the operator observes the scene from a virtual camera placed at $M_{Scope}(t)$, it appears as if 'Tissue 1', 'Tissue 2', and surgical view are rendered simultaneously creating an immersive mixed reality environment.

Figure 6:
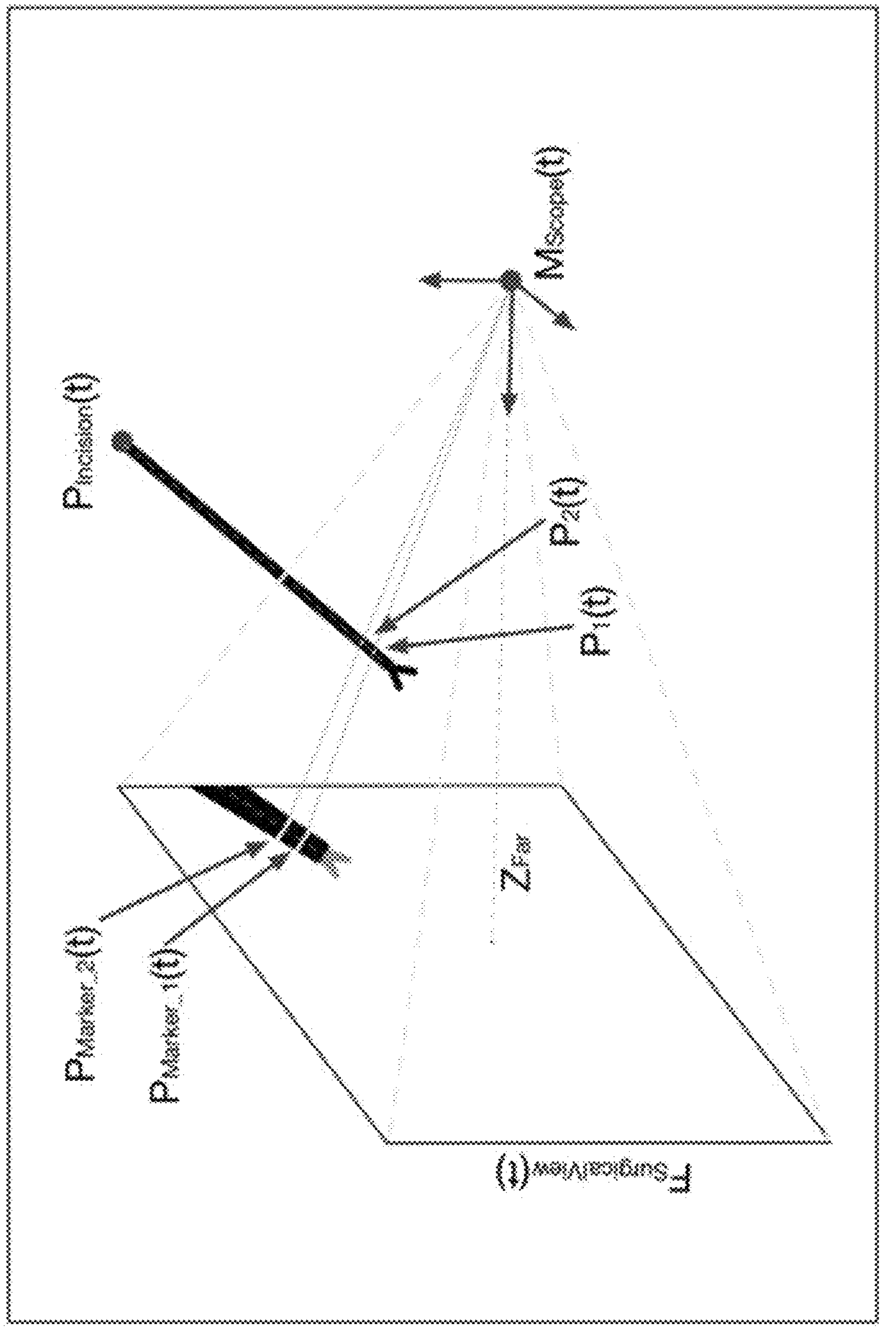
FIG. 6 illustrates a process that can be used for tracking instrument tooltips, according to various examples of the present disclosure.

The system 400 may further include a GUI module 412. The GUI module 412 is used to alter the visualization setting, scope parameters, chroma filter settings, and to set the tracking parameters for the tracking module. One aspect of objective assessment requires computing the movements of the tooltips (i.e. tooltip poses with respect to time) and in general the instrument. FIG. 6 illustrates one such process that can be used for tracking the tooltips. Two identical bands (that are distinctive from the surgical instrument) are wrapped around the cylindrical surface of the instrument. The video frame from the scope camera at time t, $F_{SurgicalView}(t)$ captures the tools with the markers as shown in the figure. Based on the relative length differences of the segment of the two bands seen in the video frame (as $P_{Marker\_1}(t)$ and $P_{Marker\_2}(t)$), the pose of the scope camera $M_{Scope}(t)$, and the fixed incision point $P_{Incision}(t)$, both the tooltips poses with respect to $M_{Scope}(t)$ can be computed. A virtual tool can also be rendered along the points $P_1(t)$ and $P_2(t)$.

Figures 7A, 7B, 7C:
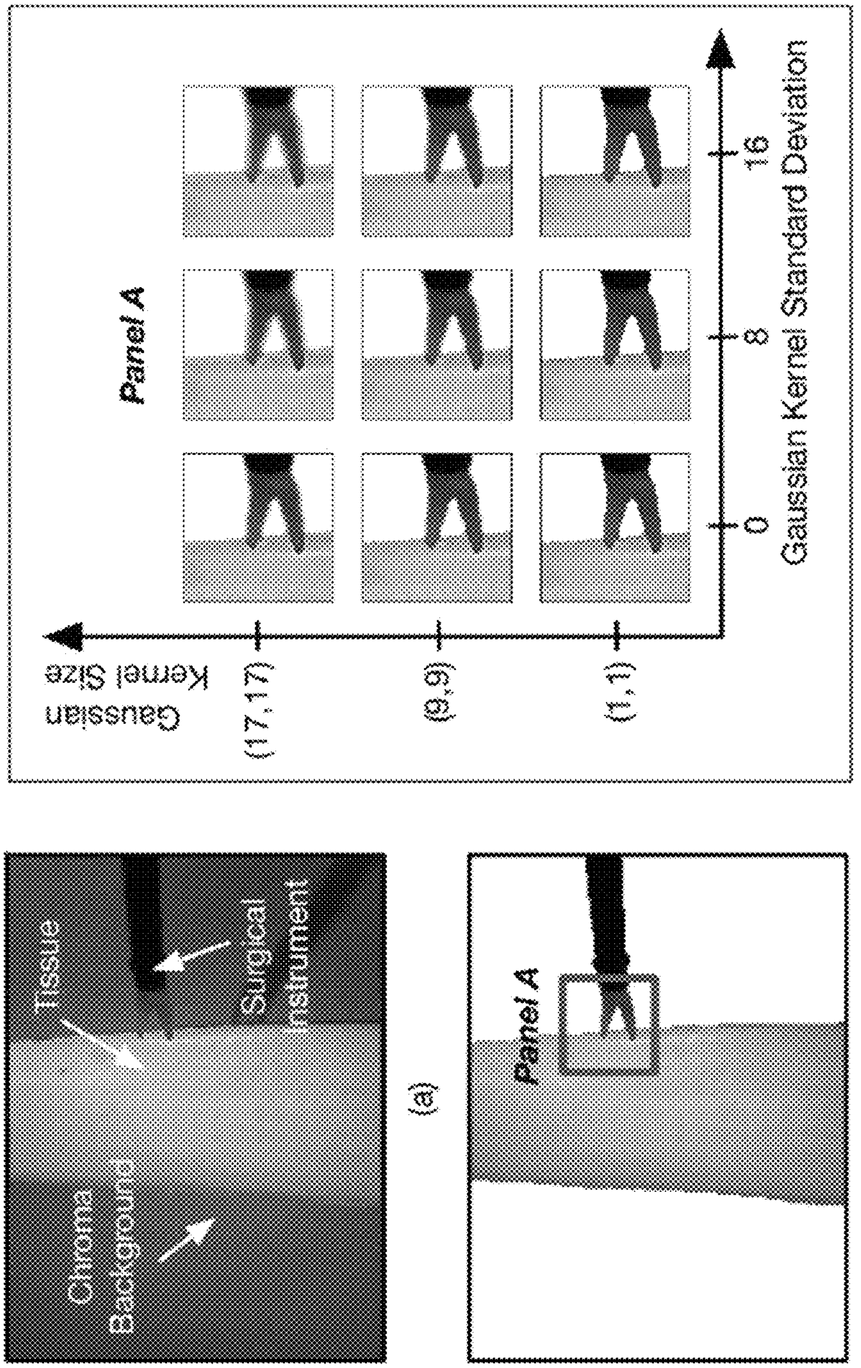
FIGS. 7A to 7C illustrate chroma background processing, according to various examples of the present disclosure.

FIGS. 7A to 7C illustrate chroma background processing, according to various examples of the present disclosure. In an example embodiment, chroma background processing shows the raw frame $F_{SurgicalView}(t)$ from the scope camera. The frame visualized three components placed in the simulator: (i) tissue at the center of the frame that the trainee will interact with, (ii) surgical instruments to be used for interaction, and (iii) green color chroma background. FIG. 7B shows the results after applying a chroma-key filter to the original frame. FIG. 7C shows the effect of applying a Gaussian blur filter with different kernel sizes and kernel standard deviation to a highlighted region (labeled as "Panel A" in FIG. 7B). It can be observed that a kernel size of (9, 9) with a standard deviation of 8 gives smooth edges for both the tissue and the surgical instruments under the ambient light setting used in the simulator.

Although the method has been described in certain specific aspects, many additional modifications and variations would be apparent to those skilled in the art. In particular, any of the various processes described above can be performed in alternative sequences and/or in parallel in order to achieve similar results in a manner that is more appropriate to the requirements of a specific application. It is therefore to be understood that the present disclosure can be practiced otherwise than specifically described without departing from the scope and spirit of the present embodiments. Thus, embodiments of the present invention should be considered in all respects as illustrative and not restrictive. It will be evident to the annotator skilled in the art to freely combine several or all of the embodiments discussed here as deemed suitable for a specific application of the invention. Throughout this disclosure, terms like "advantageous", "exemplary" or "preferred" indicate elements or dimensions which are particularly suitable (but not essential) to the invention or an embodiment thereof, and may be modified wherever deemed suitable by the skilled annotator, except where expressly required. Accordingly, the scope of the invention should be determined not by the embodiments illustrated, but by the appended claims and their equivalents.

The invention is claimed as follows:

1. A system for mixed reality surgical simulation comprising:

a simulator;

an optical tracking system;

an input device;

a visualization screen; and a simulation workstation, wherein the simulation workstation renders an augmented view on the visualization screen;

wherein the optical tracking system is configured to acquire tracking data and the simulator is configured to acquire video stream data;

wherein the input device is configured to transmit a plurality of user inputs;

wherein the simulation workstation comprises: a video module configured to receive video stream data; a tracking module configured to receive tracking data; and a user interfacing module configured to receive the plurality of user inputs;

wherein the simulation workstation further comprises a core processing module configured to process video stream data, tracking data, and the plurality of user inputs, and wherein the core processing module is configured to transmit video stream data, tracking data, and the plurality of user inputs to a graphical rendering module;

wherein the core processing module is configured to execute chroma keying on the video stream data to remove a background in the video stream data in real-time; and wherein the graphical rendering module is configured to place the video stream data with the background removed in the virtual environment at the frustum of the virtual camera and render the view on a visualization screen.

2. The system of claim 1, wherein the simulator comprises:

a scope system;

a box tracking frame;

a chroma background;

an aperture configured to receive an instrument;

a configuration table configured to receive a tissue; and an ambient light.

3. The system of claim 2, wherein the scope system includes a tracking frame.

4. The system of claim 1, wherein the simulator is a box simulator.

5. A method of mixed reality surgical simulation comprising the steps of:

positioning a simulator in front of an optical tracking system;

activating a simulation workstation, an optical tracking system, and a scope system, wherein a box tracking frame of the simulator is in a field of view of the optical tracking system;

loading a virtual tissue model onto the simulation workstation;

placing the virtual tissue model in a virtual environment based on the tracking frame of the simulator;

placing a virtual camera in the virtual environment, wherein the virtual camera matches a relative pose of a tracking frame of the scope system;

configuring a plurality of parameters using an input device;

placing a 3D-printed tissue on a configuration table of the simulator;

inserting a surgical instrument into the simulator; and performing a surgical task on the 3D-printed tissue within the simulator;

wherein the optical tracking system acquires tracking data and the simulator acquires video stream data;

wherein the input device transmits a plurality of user inputs;

wherein the simulation workstation comprises: a video module configured to receive video stream data; a tracking module configured to receive tracking data; and a user interfacing module configured to receive the plurality of user inputs;

wherein the simulation workstation further comprises a core processing module configured to process video stream data, tracking data, and the plurality of user inputs, and wherein the core processing module transmits video stream data, tracking data, and the plurality of user inputs to a graphical rendering module;

wherein the core processing module executes chroma keying on the video stream data to remove a background in the video stream data in real-time; and wherein the graphical rendering module places the video stream data with the background removed in the virtual environment at the frustum of the virtual camera and renders the view on a visualization screen.

* * * * *